United States Patent [19]

Takagawa et al.

[11] Patent Number: 5,248,809
[45] Date of Patent: Sep. 28, 1993

[54] PROCESS FOR PREPARING A POLYMERIZABLE COMPOUND HAVING BOTH POLYMERIZABLE DOUBLE BOND AND HYDROXYL GROUP

[75] Inventors: Ryozo Takagawa, Osaka; Hisaki Tanabe, Kyoto; Yoshio Eguchi, Osaka; Koichi Tsutsui, Kyoto, all of Japan

[73] Assignee: Nippon Paint Co., Ltd., Osaka, Japan

[21] Appl. No.: 432,873

[22] Filed: Nov. 7, 1989

[30] Foreign Application Priority Data

Nov. 7, 1988 [JP] Japan ................. 63-280968

[51] Int. Cl.$^5$ .............. C07C 69/66; C08F 20/26; C08G 73/00
[52] U.S. Cl. ................ 560/185; 526/320; 528/354; 528/358; 528/368; 560/183; 525/450
[58] Field of Search .......... 526/320; 560/185, 183; 528/354, 358, 368

[56] References Cited

U.S. PATENT DOCUMENTS 4,504,635  3/1985  Weber et al. ............. 528/355
4,691,045  9/1987  Fukuchi et al. ............ 526/320
4,983,689  1/1991  Yu ......................... 526/320

Primary Examiner—Paul R. Michl
Assistant Examiner—Tae H. Yoon
Attorney, Agent, or Firm—Wenderoth, Lind & Ponack

[57] ABSTRACT

A process for preparing a polymerizable compound of the formula:

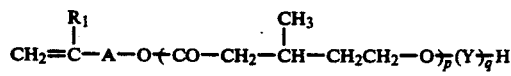

or a polymerizable compound of the formula:

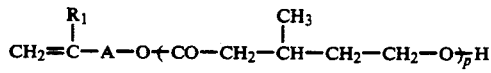

is provided. These formed compounds are useful for the preparation of an acrylic resin which is low in viscosity and capable of forming a coating with excellent flexibility, weather resistance and water resistance.

10 Claims, No Drawings

PROCESS FOR PREPARING A POLYMERIZABLE COMPOUND HAVING BOTH POLYMERIZABLE DOUBLE BOND AND HYDROXYL GROUP

FIELD OF THE INVENTION

The present invention relates to a process for preparing a novel polymerizable compound having in its molecule a structure of the formula:

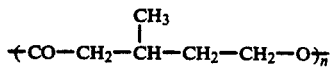

The invention also concerns a coating composition comprising an acrylic resin-derived therefrom, which is low in viscosity and capable of forming a coating with excellent flexibility, weather resistance and water resistance.

DESCRIPTION OF RELATED

A bake-curing type acrylic resin used in a coating composition usually contains crosslinkable hydroxyl groups. Such a resin, from the standpoint of air-pollution problems, should preferably be suitable for high solid paint or aqueous paint. Especially, for a high solid paint, the resin must have a low viscosity.

Heretofore, for the lowering in viscosity of an acrylic resin, attempts have been made to lower the glass transition point (Tg) of the acrylic resin by the selective use of such monomers as acrylates and methacrylates, each bearing a considerably long carbon chain, or to lower the molecular weight of the resin.

However, in the former, a comparatively larger quantity of acrylate or methacrylate is required, resulting in the decrease in crosslinking sites and hence crosslinking reactivity of the formed resin. In the latter, the low molecular weight resinous portion having no functional group is necessarily increased, resulting in the decrease in crosslinking reactivity and the formation of a coating with inferior film properties. Thus, there is a limit in the lowering in viscosity of an acrylic resin and it has been believed to be very difficult to satisfy both requirements, i.e. lower viscosity and high crosslinking reactivity, at the same time. Recently, as a measure for giving desired low viscosity, flexibility and crosslinking reactivity to an addition polymer as acrylic resin, attempts have been made to prepare a polymerizable macromer by the ring-opening polymerization of lactone onto a hydroxyl containing acrylic monomer and effect copolymerization of thus obtained macromer with other acrylic monomers.

In U.S. Pat. No. 4,504,635, Japanese Patent Publication (unexamined) Nos. 57-185236 and 61-43623, there is disclosed a method wherein ε-caprolactone is ring-opening polymerized onto 2-hydroxyethyl(meth)acrylate in the presence of stannic catalyst. However, thus obtained ε-caprolactone (meth)acrylates show a crystallization tendency and when the polymerization degree of ε-caprolactone exceeds over the limit of 4 to 5, the resulting products are solid at room temperatures. Therefore, acrylic polymers or copolymers derived therefrom likewise show the similar tendency depending on the amount of such (meth)acrylate contained. As a consequence, there is necessarily a certain difficulty in handling, insufficient viscosity and inferior hydrolysis resistance and alkaline resistance.

Japanese Patent Publication (unexamined) Nos. 60-55026, 60-26019 and 60-120714 disclose a process for the preparation of polyester polyol having the structure of

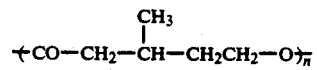

comprising ring-opening polymerizing β-methyl-δ-valerolactone onto the starting material of low molecular weight compound as ethylene glycol.

According to the disclosed process, it is possible to obtain a polyol which is liquid at room temperatures, has a low viscosity and is excellent in hydrolysis resistance. However, since it has no polymerization reactive group, it cannot be used for the preparation of radical polymer for coating use. It is, therefore an object of the invention to provide a novel class of compounds each having both an end polymerizable group and a crosslinkable hydroxyl group, as well as a non-crystalline, flexible structure of the formula:

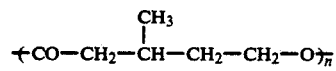

whose viscosities are sufficiently low and which are useful for the preparation of an acrylic resin capable of forming a coating which are excellent in lower viscosity, weather resistance, water resistance, hydrolysis resistance, alkaline resistance and crosslinking reactivity.

It is an additional object of this invention is to provide an industrially attractive process for the preparation of said polymerizable compound, in respect to reaction speed and reaction yield. A further object of the present invention is to provide an acrylic resin composition whose viscosity is very low and which has a high crosslinking reactivity and can be used as a bake curing type film-forming resin, capable of forming a coating with excellent hydrolysis resistance, alkaline resistance, water resistance and weather resistance as well as flexibility, toughness and elasticity, and also as a molding material capable of forming a molded product having a high rubber elasticity.

BRIEF SUMMARY OF THE INVENTION

According to the invention, the abovementioned objects are attained by

1. A process for preparing a polymerizable compound of the formula:

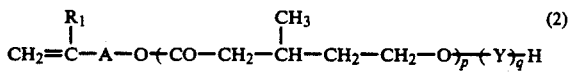 (2)

wherein $R_1$ is hydrogen atom or methyl; A represents a group represented by either one of the formula:

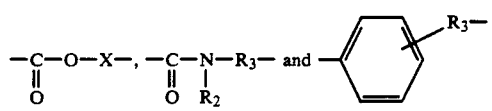

in which

X is an alkylene having 2 to 4 carbon atoms or a group represented by either one of the formulae:

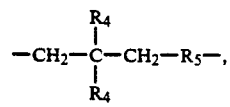

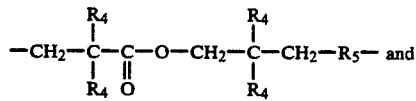

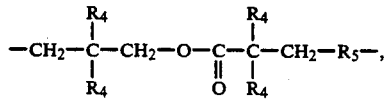

$R_2$ is hydrogen atom or an alkyl having 1 to 10 carbon atoms; $R_3$ is a group represented by either one of the formula:

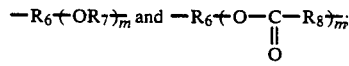

$R_4$ is the same or different radicals and each represents a lower alkyl having 1 to 4 carbon atoms; $R_5$ is a group represented by the formula:

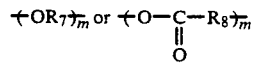

$R_6$ is an alkylene having 1 to 4 carbon atoms; $R_7$ is an alkylene having 2 to 4 carbon atoms; $R_8$ is an alkylene having 2 to 7 carbon atoms; m is 0 or an integer of from 1 to 4; and Y is a group represented by either one of the formula:

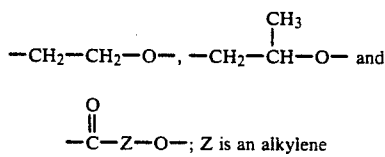

having 2 to 7 carbon atoms; p is an integer of from 1 to 100; and q is an integer of from 1 to 5 comprising ring-opening addition polymerizing 1 to 100 moles of β-methyl-δ-valerolactone to one mole of a compound having both polymerizable double bond and hydroxyl group represented by the formula:

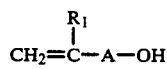

(1)

(in which $R_1$ and A each has the same meaning as defined above) in the presence of a ring-opening addition polymerization catalyst, and then effecting a ring-opening addition of 1 to 5 moles of alkylene oxide or a cyclic ester to thus obtained compound.

2. A process for preparing a polymerizable compound of the formula:

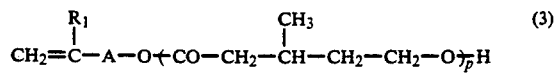

(3)

wherein $R_1$ is hydrogen atom or methyl; A represents a group represented by either one of the formula:

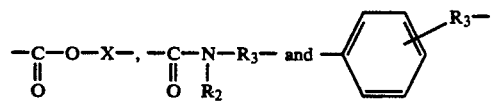

in which X is an alkylene having 2 to 4 carbon atoms or a group represented by either one of the formula:

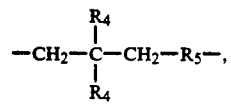

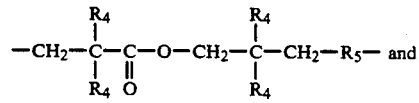

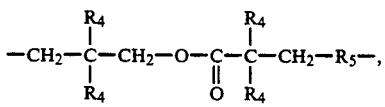

$R_2$ is hydrogen atom or an alkyl having 1 to 10 carbon atoms; $R_3$ is a group represented by either one of the formula:

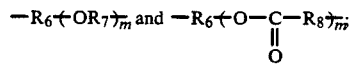

$R_4$ is the same or different radicals and each represents a lower alkyl having 1 to 4 carbon atoms; $R_5$ is a group represented by the formula:

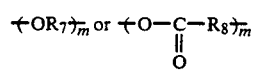

$R_6$ is an alkylene having 1 to 4 carbon atoms; $R_7$ is an alkylene having 2 to 4 carbon atoms; $R_8$ is an alkylene having 2 to 7 carbon atoms; m is 0 or an integer of from 1 to 4; comprising ring-opening addition polymerizing 1 to 100 moles of β-methyl-δ-valerolactone to one mole of a compound having both polymerizable double bond and hydroxyl group represented by the formula:

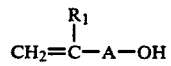

(1)

(in which $R_1$ and A each has the same meaning as defined above) in the presence of a ring-opening addition polymerization catalyst.

3. A coating composition comprising an acrylic resin obtained by the polymerization of a monomer mixture of 20 to 100 mole % of the polymerizable compound stated in either one of the claims 1 to 6 and 80 to 0 mole % of other α,β-ethylenically unsaturated monomer and having a number average molecular weight of 1,000 to 100,000.

In a series of studies on acrylic and methacrylic derivatives, the inventors have tried to effect ring-opening addition polymerization of various cyclic lactones on a ω-hydroxyl bearing monomer, to introduce comparatively long methylene chain into the monomer through ester bonding, thereby improving flexibility and adhesion properties thereof. However, most of the cyclic lactones tested had problems in that the formed polymerizable compounds were of crystalline nature and the vinyl polymers derived from said polymerizable compounds showed inferior hydrolysis resistance and alkaline resistance. And only β-methyl-δ-valerolactone gave the desired polymerizable compounds which are easily handleable liquid at room temperatures and well resistive toward hydrolysis and whose end hydroxyl groups are very reactive and well suitable for the present objects. However, in the reaction of actual ring-opening addition polymerization of β-methyl-δ-valerolactone on a ω-hydroxyl group containing compound, it was found that when hydroxyalkyl (meth) acrylate as 2-hydroxylethylmethacrylate is used as a starting material, there easily occurs side reactions and in order to obtain the intended product, it is essential that the reaction be carried out at a temperature of −20° C. or less. The inventors' further studies revealed that even when the desired compounds were obtained, certain device should be made to prevent thermal depolymerization of the product compound, otherwise β-methyl-δ-valerolactone units would be disconnected under heating conditions one by one and flexibility of the compound would be lost out finally. The inventors have found that certain alkyleneoxides or cyclic esters are very effective for this end. On the basis of these findings, the present inventions have been made.

DETAILED DESCRIPTION OF THE INVENTION

In the present invention, a compound represented by the formula:

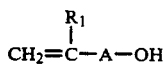

is used as a starting material having both a reactive double bond and an end hydroxyl group.

In the above-said formula, $R_1$ is hydrogen atom or methyl; A represents a group represented by either one of the formula:

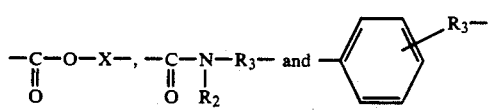

in which X is an alkylene having 2 to 4 carbon atoms or a group represented by either one of the formula:

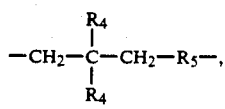

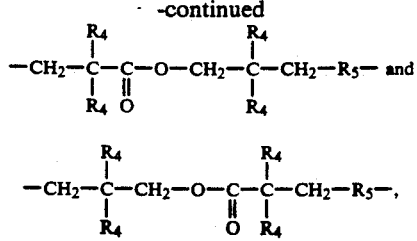

$R_2$ is hydrogen atom or an alkyl having 1 to 10 carbon atoms; $R_3$ is a group represented by either one of the formulas:

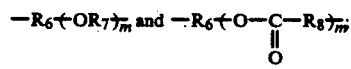

$R_4$ is the same or different radicals and each represents a lower alkyl having 1 to 4 carbon atoms; $R_5$ is a group represented by the formula:

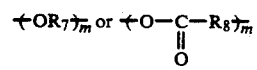

$R_6$ is an alkylene having 1 to 4 carbon atoms; $R_7$ is an alkylene having 2 to 4 carbon atoms; $R_8$ is an alkylene having 2 to 7 carbon atoms; and m is 0 or an integer of from 1 to 4.

Such compounds can be easily prepared by starting with ω-hydroxy alkyl acrylate or methacrylate, acrylic or methacrylic amide or styrene derivatives and freely available at the market.

In this invention, to the abovementioned starting compound, 1 to 100 times moles, preferably 1 to 50 times moles of β-methyl-δ-valerolactone are ring-opening addition polymerized in the presence of ring-opening addition polymerization catalyst as, for example, mineral acids (e.g. sulfuric acid, phosphoric acid and the like), alkali metals (e.g. lithium, sodium, potassium and the like), metal alkoxides (e.g. t-butoxy potassium and the like), and alkyl metal compounds (e.g. n-butyl lithium and the like). The amount of catalyst may be in general in a range of from 0.01 to 1 mole per mole of the starting compound.

The reaction may be carried out in the absence or presence of an inert solvent having no active hydrogen atom. Preferable solvent is an anhydrous inert solvent and especially tetrahydrofuran. The reaction, however, should be carried out in an inert gaseous atmosphere as nitrogen, helium, argon and the like and at a temperature not exceeding 200° C. This is because the reaction is a exothermic reaction and stability of β-methyl-δ-valerolactone is spoiled at a temperature of more than 200° C. Usually, the required reaction time is from 10 minutes to several hours and the reaction is stopped at that stage by adding an aqueous mineral acid solution or water.

The reaction product is then extracted with an appropriate solvent and purified according to usual procedures to give the desired polymerizable compound as a pale yellow to colorless viscous liquid.

At that time, if the amount of β-methyl-δ-valerolactone exceeds over 100 moles per mole of ω-hydroxyl group containing compound, the synthesis of the desired compound will become difficult because of undesired increase in viscosity of the reaction product. At the same time, with the increase in molecular weight, hydroxyl value of the product will become low and hence such product is unsuitable for the synthesis of coating use resin.

Therefore, for the purpose of obtaining polymerizable compounds for coating use resin, the amount of β-methyl-δ-valerolactone should be limited to 1 to 100 times moles, preferably 1 to 50 times moles, and most preferably 1 to 20 times moles, per mole of hydroxyl containing compound. As a resinous vehicle of a curing type coating composition, OH value of a film forming resin should preferably be controlled in an appropriate range capable of reacting with a crosslinking agent and resulting in a cured coating with improved properties. In this connection, it has been found that the polymerization degree of said β-methyl-δ-valerolactone should preferably be in a range of 1 to 20. If it is more than 20, there is a tendency that deficient curing occurs due to an excessive increase in OH value. Therefore, for obtaining a resin to be used in a curing type coating composition, the amount of β-methyl-δ-valerolactone should be advantageously limited to 1 to 20 times moles per mole of hydroxy containing compound.

As already stated, the inventors have also found that thus obtained compounds are fairly stable at a temperature of 100° C. or less, but easily depolymerized at a higher temperature. Therefore, in the present invention, thus obtained compounds are then subjected to ring-opening addition reaction with 1 to 5 moles of alkylene oxide or cyclic ester, thereby adding such members at the end portion and preventing the above-said depolymerization at a higher temperature possibly encountered at the baking stage of coating use resin. The term "cyclic ester" as used herein shall mean lactones other than β-methyl-δ-valerolactone and preferably having up to 6 carbon atoms. Thus obtained compounds represented by the formula:

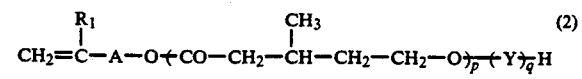

(in which $R_1$, A, Y, p and q each has the same meanings as defined hereinbefore) each has a polymerizable double bond, a flexible long methylene chain and an end hydroxyl group which is very reactive for crosslinking reaction, is hardly affected by depolymerization at a higher temperature of 100° C. or more and can maintain its low viscous liquid state irrespective of comparatively high molecular weight, and therefore, is very useful as a starting material for the synthesis of vinyl resins and especially vinyl resins for coating use. The intermediate compounds obtained by the reaction of a compound represented by the formula:

and β-methyl-δ-valerolactone, which are not yet reacted with alkyleneoxides or cyclic esters, are all novel compounds. Among them, particularly preferably members are as follows: A polymerizable compound represented by the formula:

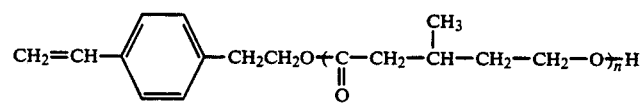

in which n is an integer of from 1 to 100.

A polymerizable compound represented by the formula:

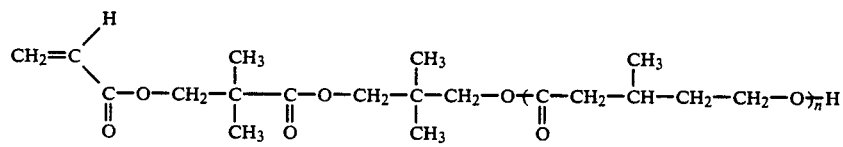

in which n is an integer of from 1 to 100.

A polymerizable compound represented by the formula:

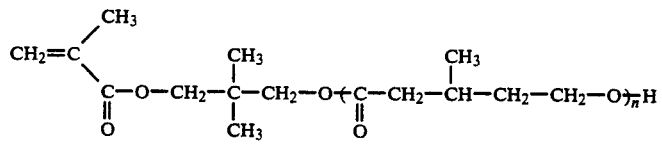

in which n is an integer of from 1 to 100.

A polymerizable compound represented by the formula:

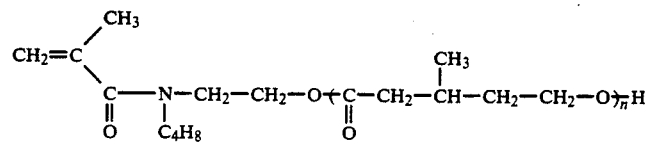

in which n is an integer of from 1 to 100.

The present polymerizable compounds and above-mentioned their intermediate compounds can be polymerized with other α,β-ethylenically unsaturated monomers to give vinyl resins and especially coating use vinyl or acrylic resins. At the time when the abovementioned intermediate compounds are selected as copolymerization monomers, caution should be paid, at any stages of preparation of resin, preparation and application of coating composition and its baking, not to use a higher temperature of 100° C. or more. Otherwise, there will occur depolymerization of β-methyl-δ-valerolactone units, as mentioned hereinbefore.

In order to get a vinyl or acrylic resin especially useful for coating application, it has also been found that the present polymerizable compound and other α,β-ethylenically unsaturated monomer(s) should preferably be selected in a ratio, in terms of molar % ratio, of 20/80 to 100/0, to obtain a resin having a number average molecular weight of 1,000 to 100,000. Such resin has a low viscosity, is highly reactive for crosslinking reaction and can give a coating with excellent hydrolysis resistance, water resistance, alkaline resistance and weather resistance, which has also the characteristics of softness and toughness.

The invention shall be now more fully explained in the following Examples. Unless otherwise being stated, all parts and % are by weight.

EXAMPLE 1

Into a 1000 ml flask fitted with a stirrer, a dropping funnel, a thermometer and a gas inlet tube, were placed, after flashing the flask with a nitrogen gas, 250 g of dried tetrahydrofuran (hereinafter abbreviated as THF) and 50 g of p-hydroxyethyl styrene and the mixture was, while stirring and introducing nitrogen gas, added gradually with 17 ml of 1.6 moles n-BuLi hexane solution. After ceasing exothermic reaction, the reaction mixture was cooled to 5° C. and 116 g of β-methyl-δ-valerolactone (hereinafter abbreviated as MVL) were drop-wise added from the dropping funnel, while keep stirring, to the reaction mixture in 1 hour. The reaction was further continued under the same conditions for additional 30 minutes and then stopped by adding 27 ml of 1N HCl aqueous solution to the reaction mixture. The content was then taken in a 1000 ml separating funnel, added with 200 ml of ether and 100 ml of deionized water, and after adjusting pH of its aqueous layer to 12 or more with a 20% aqueous NaOH solution, the combined was vigorously shaken and then stationary kept stand. Aqueous layer was then removed off, and the remainder was again added with 100 ml of deionized water, neutralized with a 10% aqueous HCl solution, shaken well and kept stand stationary and the aqueous layer was again removed off. Thereafter, the organic layer was washed several times with deionized water, dried over anhydrous sodium sulfate and ether and THF solvents were completely removed off by using a rotary evaporator at 60° C. and under reduced pressure to obtain 115 g of a pale yellow, clear, viscous liquid a-1.

$^1$H-NMR and $^{13}$C-NMR tests were carried out with the liquid a-1 and it was found that there was no absorption peak of MVL. From the chemical shifts of said $^1$H-NMR and $^{13}$C-NMR, it was confirmed that the liquid was a polymer comprising p-hydroxyethyl styrene connected with several units of MVL through ring-opening addition reaction thereof. It was also found that an average polymerization degree of MVL calculated from integral values of $^1$H-NMR and $^{13}$C-NMR signals was 3 and its viscosity was 1.6 poises.

EXAMPLES 2 TO 5

Various polymerizable compounds were prepared as in Example 1 using the materials shown in Table 1, and their average polymerization degrees of MVL and viscosities were shown in Table 1.

TABLE 1

| | Example | | | |
|---|---|---|---|---|
| | 2 | 3 | 4 | 5 |
| compound | a-2 | a-3 | a-4 | a-5 |
| p-hydroxyethyl styrene (g) | 50 | 50 | 16.7 | 8.3 |
| tetrahydrofuran (g) | 250 | 250 | 83 | 42 |
| n-BuLi* (ml) | 16.9 | 16.9 | 5.6 | 2.8 |
| MVL (g) | 385 | 193 | 321 | 257 |
| 1N—HCl (ml) | 27 | 27 | 9 | 4.5 |
| average degree of polymerization of MVL | 11 | 5 | 27 | 45 |
| viscosity (poise) | 7.0 | 3.6 | 36.9 | 83.6 |
| yield (g) | 305 | 165 | 240 | 193 |

*1.6 moles hexane solution (hereinafter the same)

EXAMPLE 6

As in Example 1, 50 g of p-hydroxyethyl styrene and 3.8 g of t-butoxy potassium were added under stirring to 500 g of THF and after ceasing an exothermic reaction, the reaction mixture was cooled to 5° C. The, while keep stirring, 193 g of MVL were drop-wise added from a dropping funnel to the flask in 1 hour, the mixture was further reacted for 30 minutes and the reaction was stopped by adding 27 ml of 1N HCl solution. Thereafter, the reaction mixture was treated in the same way as in Example 1 to obtain 183 g of pale yellow viscous liquid (a-6). Average degree of polymerization of MVL was 5 and viscosity was 3.4 poises.

EXAMPLE 7

Using the same procedures as stated in Example 1 with the smae materials as used in Example 3, polymerization of MVL was effected on p-hydroxyethylstyrene. Thereafter, 58 g of ε-caprolactone were drop-wise added in 30 minutes and reacted for 30 minutes. Then, 27 ml of 1N HCl solution were added to stop the reaction and the reaction mixture was treated in the same way as stated in Example 1 to obtain 203 g of pale yellow clear, viscous liquid (a-7). The liquid was a polymer comprising p-hydroxyethylstyrene to which MVL units were ring-opening polymerized and average 1 mole ε-caprolactone was further added thereonto. Average degree of polymerization of MVL was 5 and viscosity was 3.8 poises.

EXAMPLE 8

Using the same procedures as stated in Example 1 with the same materials as used in Example 4, polymerization of MVL was effected on p-hydroxyethylstyrene. Thereafter, 58 g of ε-caprolactone were drop-wise added in 30 minutes and reacted for 30 minutes. Then, 27 ml of 1N HCl solution were added to stop the reaction and the reaction mixture was treated in the same way as stated in Example 1 to obtain 280 g of pale yellow clear, viscous liquid (a-8). The liquid was a polymer comprising p-hydroxyethylstyrene to which MVL units were ring-opening polymerized and average 1 mole ε-caprolactone was further added thereonto. Average degree of polymerization of MVL was 27 and viscosity was 38.1 poises.

EXAMPLE 9

Using the same procedures as stated in Example 1 with the same materials as used in Example 5, polymerization of MVL was effected on p-hydroxyethylstyrene. Thereafter, 145 g of propyleneoxide were drop-wise added in 30 minutes and reacted for 30 minutes. Then, 27 ml of 1N HCl solution were added to stop the reaction and the reaction mixture was treated in the same way as stated in Example 1 to obtain 440 g of pale yellow clear, viscous liquid (a-9). The liquid was a polymer comprising p-hydroxyethylstyrene to which MVL units were ring-opening polymerized and average 2 mole propylene oxide were further added thereonto. Average degree of polymerization of MVL was 5 and viscosity was 3.9 poises.

EXAMPLE 10

Using the same procedures as stated in Example 1 with the same materials as used in Example 2, polymerization of MVL was effected on p-hydroxyethylstyrene. Thereafter, 58 g of ε-caprolactone were drop-wise added in 30 minutes and reacted for 30 minutes. Then, 27 ml of 1N HCl solution were added to stop the reaction and the reaction mixture was treated in the same way as stated in Example 1 to obtain 280 g of pale yellow clear, viscous liquid (a-10). The liquid was a polymer comprising p-hydroxyethylstyrene to which MVL units were ring-opening polymerized and average 1 mole ε-caprolactone was further added thereonto. Average degree of polymerization of MVL was 11 and viscosity was 7.3 poises.

EXAMPLE 11

As in Example 1, 8.3 g of p-hydroxyethylstyrene were dissolved in 42 g of THF and to this, under stirring, 2.8 ml of 1.6 moles n-BuLi hexane solution were added and after ceasing an exothermic reaction, the reaction mixture was cooled to 5° C. Then, while keep stirring, 570 g of MVL were drop-wise added from a dropping funnel to the flask in 1 hour, the mixture was further reacted for 30 minutes and the reaction was stopped by adding 4.5 ml of 1N HCl solution. Thereafter, the reaction mixture was treated in the same way as in Example 1 to obtain 465 g of pale yellow viscous liquid(a-11). Average degree of polymerization of MVL was 81 and viscosity was 122 poises.

EXAMPLE 12

As in Example 1, 50 g of hydroxypivalic acid neopentyl glycol ester monoacrylate were dissolved in 250 g of THF and to this, under stirring, 9.7 ml of 1.6 moles n-BuLi hexane solution were added and after ceasing an exothermic reaction, the reaction mixture was cooled to 5° C. Then, while keep stirring, 40 g of MVL were drop-wise added from a dropping funnel to the flask in 1 hour, the mixture was further reacted for 30 minutes and the reaction was stopped by adding 15 ml of 1N HCl solution. Thereafter, the reaction mixture was treated in the same way as in Example 1 to obtain 63 g of clear viscous liquid(b-1). Average degree of polymerization of MVL was 2 and viscosity was 0.7 poises.

EXAMPLE 13

The same procedures as stated in Example 12 were repeated excepting changing the adding amount of MVL to 200 g to obtain 190 g of a clear viscous liquid (b-2). Average degree of polymerization of MVL was 10 and viscosity was 6.3 poises.

EXAMPLE 14

As in Example 1, 10 g of hydroxypivalic acid neopentyl glycol ester monoacrylate were dissolved in 50 g of THF and to this, under stirring, 1 ml of 1.6 moles n-BuLi hexane solution were added and after ceasing an exothermic reaction, the reaction mixture was cooled to 5° C. Then, while keep stirring, 180 g of MVL were drop-wise added from a dropping funnel to the flask in 1 hour, the mixture was further reacted for 30 minutes and the reaction was stopped by adding 1.5 ml of 1N HCl solution. Thereafter, the reaction mixture was treated in the same way as in Example 1 to obtain 140 g of clear viscous liquid(b-3). Average degree of polymerization of MVL was 43 and viscosity was 80.5 poises.

EXAMPLE 15

As in Example 1, 50 g of hydroxypivalic acid neopentyl glycol ester monoacrylate were dissolved in 250 g of THF and to this, under stirring, 9.7 ml of 1.6 moles n-BuLi hexane solution were added and after ceasing an exothermic reaction, the reaction mixture was cooled to 5° C. Then, while keep stirring, 100 g of MVL were drop-wise added from a dropping funnel to the flask in 1 hour, after completion of said addition, 35 g of ε-caprolactone were drop-wise added in 30 minutes, the mixture was further reacted for 30 minutes and the reaction was stopped by adding 15 ml of 1N HCl solution. Thereafter, the reaction mixture was treated in the same way as in Example 1 to obtain 120 g of clear viscous liquid (b-4). This liquid (b-4) is a polymer comprising hydroxypivalic acid neopentyl glycol monoacrylate, to which MVL units were ring-opning addition polymerized and further added with average 1 mole of ε-caprolactone. Average degree of polymerization of MVL was 5 and viscosity was 3.2 poises.

EXAMPLE 16

As in Example 1, 50 g of neopentyl glycol ester monomethacrylate were dissolved in 250 g of THF and to this, under stirring, 14.5 ml of 1.6 moles n-BuLi hexane solution were added and after ceasing an exothermic reaction, the reaction mixture was cooled to 5° C. Then, while keep stirring, 100 g of MVL were drop-wise added from a dropping funnel to the flask in 1 hour, the mixture was further reacted for 30 minutes and the reaction was stopped by adding 23 ml of 1N HCl solution. Thereafter, the reaction mixture was treated in the same way as in Example 1 to obtain 113 g of clear viscous liquid(c-1). Average degree of polymerization of MVL was 3 and viscosity was 1.7 poises.

EXAMPLE 17

As in Example 16, 10 g of neopentyl glycol ester monomethacrylate were dissolved in 50 g of THF and to this, under stirring, 2.9 ml of 1.6 moles n-BuLi hexane solution were added and after ceasing an exothermic reaction, the reaction mixture was cooled to 5° C. Then, while keep stirring, 300 g of MVL were drop-wise added from a dropping funnel to the flask in 1 hour, the mixture was further reacted for 30 minutes and the reaction was stopped by adding 4.7 ml of 1N HCl solution. Thereafter, the reaction mixture was treated in the same way as in Example 1 to obtain 242 g of clear viscous liquid(c-2). Average degree of polymerization of MVL was 46 and viscosity was 83.4 poises.

EXAMPLE 18

As in Example 16, 50 g of neopentyl glycol ester monomethacrylate were dissolved in 250 g of THF and to this, under stirring, 14.5 ml of 1.6 moles n-BuLi hexane solution were added and after ceasing an exothermic reaction, the reaction mixture was cooled to 5° C. Then, while keep stirring, 200 g of MVL were drop-wise added from a dropping funnel to the flask in 1 hour, after completion of said addition, 51 g of ε-caprolactone were drop-wise added in 30 minutes, the mixture was further reacted for 30 minutes and the reaction was stopped by adding 23 ml of 1N HCl solution. Thereafter, the reaction mixture was treated in the same way as in Example 1 to obtain 228 g of clear viscous liquid (c-3). This liquid (c-3) is a polymer comprising neopentyl glycol monomethacrylate, to which MVL units were ring-opning addition polymerized and further added with average 1 mole of ε-caprolactone. Average degree of polymerization of MVL was 6 and viscosity was 4.4 poises.

EXAMPLE 19

As in Example 1, 50 g of N-(n-butyl)-N-(2hydroxyethyl) methacrylamide were dissolved in 250 g of THF and to this, under stirring, 13.5 ml of 1.6 moles n-BuLi hexane solution were added and after ceasing an exothermic reaction, the reaction mixture was cooled to 5° C. Then, while keep stirring, 62 g of MVL were drop-wise added from a dropping funnel to the flask in 1 hour, the mixture was further reacted for 30 minutes and the reaction was stopped by adding 21.6 ml of 1N HCl solution. Thereafter, the reaction mixture was treated in the same way as in Example 1 to obtain 93 g of clear viscous liquid(d-1). Average degree of polymerization of MVL was 2 and viscosity was 0.9 poises.

EXAMPLE 20

As in Example 19, 10 g of N-(n-butyl)-N-(2hydroxyethyl) methacrylamide were dissolved in 50 g of THF and to this, under stirring, 2.7 ml of 1.6 moles n-BuLi hexane solution were added and after ceasing an exothermic reaction, the reaction mixture was cooled to 5° C. Then, while keep stirring, 247 g of MVL were drop-wise added from a dropping funnel to the flask in 1 hour, the mixture was further reacted for 30 minutes and the reaction was stopped by adding 4.3 ml of 1N HCl solution. Thereafter, the reaction mixture was treated in the same way as in Example 1 to obtain 193 g of clear viscous liquid(d-2). Average degree of polymerization of MVL was 42 and viscosity was 78.6 poises.

EXAMPLE 21

As in Example 19, 50 g of N-(n-butyl)-N-(2hydroxyethyl) methacrylamide were dissolved in 250 g of THF and to this, under stirring, 21.6 ml of 1.6 moles n-BuLi hexane solution were added and after ceasing an exo-thermic reaction, the reaction mixture was cooled to 5° C. Then, while keep stirring, 154 g of MVL were drop-wise added from a dropping funnel to the flask in 1 hour, after elapsing 30 minutes from the completion of said addition, 47 g of ε-caprolactone were drop-wise added in 30 minutes, the mixture was further reacted for 30 minutes and the reaction was stopped by adding 21.6 ml of 1N HCl solution. Thereafter, the reaction mixture was treated in the same way as in Example 1 to obtain 188 g of clear viscous liquid(d-3). This liquid (d-3) is a polymer comprising N-(n butyl)-N-(2-hydroxyethyl)-methacrylamide, to which MVL units are ring-opnening addition polymerized and further added with average 1 mole of ε-caprolactone. Average degree of polymerization of MVL was 5 and viscosity was 3.7 poises.

EXAMPLE 22

Into a reaction vessel fitted with a stirrer, a thermometer, a reflux condenser, a nitrogen gas inlet tube and a dropping funnel, were placed 80 parts of Solvensso-100 (trademark, aromatic solvent, manufactured by Shell Oil Co.) and 10 parts of xylene and the mixture was, while introducing a nitrogen gas, heated to 140° to 150° C. To this, a mixture of 70 parts of the polymerizable compound (a-7) obtained in Example 7, 30 parts of methyl methacrylate and 5 parts of t-butylperoxy-2-ethylhexanoate was drop-wise added at a constant speed from the dropping funnel in 3 hours. After completion of said addtion, the mixture was maintained at the same temperature for 30 minutes, drop-wise added at a constant speed with a mixture of 0.5 part of t-butyl-peroxy-2-ethylhexanoate and 10 parts of xylene in 30 minutes, aged at 140° to 150° C. for 1 hour, and allowed to cool. Solvent was removed by using an evaporator to give a solution of defined solid content and thus obtained a resin solution (A-1) having a solid content of 90.1% and a viscosity of $Z_1$. Mole % of the polymerizable compound contained in the polymer of this resin solution was calculated to be 21.9%.

EXAMPLES 23 TO 31 AND COMPARATIVE EXAMPLES 1 TO 2

The same procedures as stated in Example 22 were repeated with the materials shown in Table 2 to obtain resin solutions A-2 to A-10 and B-1 to B-2. Solid contents and viscosity of the respective resin solution are shown in Table 4.

EXAMPLE 32

Using the same apparatus and method as stated in Example 22, 80 parts of methylisobutylketone and 10 parts of xylene were placed in a reactor, and the mxiture was heated, while introducing a nitrogen gas, to 90° to 95° C. To this, a mixture of 70 parts of the polymerizable compound (a-3) obtained in Example 3, 15 parts of methyl methacrylate, 15 parts of n-butylacrylate and 5 parts of azobisisobutyronitrile was dropwise added from the dropping funnel and a constant speed in 3 hours. After completion of said addition, the mixture was maintained at the same temperature for 30 minutes and then added drop-wise a mixture of 0.5 part of azobisisobutyronitrile and 10 parts of xylene in 30 minutes. Thereafter, the combined was aged at 90° to 95° C. for 1 hour and allowed to cool. Solvent was removed by using an evaporator so as to give a defined solid content and thus obtained a resin solution (A-11) having a solid content of 90.2% and a viscosity of $Z_1$ to $Z_2$. Mole % of the polymerizable compound contained in the polymer of this resin solution was calculated and it was found to be 27.6%.

EXAMPLES 33 TO 37

Using the materials shown in Table 3 and following the procedures stated in Example 32, various resin solutions A-12 to A-16 were prepared. Solid contents and viscosities of these resin solutions were shown in Table 5.

EXAMPLE 38

50 parts of the resin solution A-1 obtained in Example 22, 32 parts of U-ban 20N-60(trademark, butyrated melamine, manufactured by Mitui Tohatu K.K.) and 3.2 parts of 40% p-toluene sulfonic acid isopropylalcohol solution (hereinafter abbreviated as PTS solution) were taken in a stainless steel vessel and mixed and stirrered well by means of disper to obtain a coating composition P-1. This composition was applied by using a bar coater onto a tin plate previously degreased and baked at 140° C. for 30 minutes to obtain a cured coating. Finishing appearance, curing and film properties were evaluated and test results were shown in Table 6.

EXAMPLES 39 TO 42

Coating compositions P-2 to P-5 each was prepared from 50 parts of either one of the resin solutions A-2 to A-5 obtained in Examples 23 to 26, 32 parts of U-ban 20-N-60 and 3.2 parts of PTS solution as in Example 38 and cured coatings were prepared therefrom and evaluated as in Example 38. Test results are shown in Table 6.

EXAMPLE 43

The same procedures as stated in Example 38 were repeated using a coating composition P-6 prepared by using 53 parts of the resin solution A-6 obtained in Example 27, 32 parts of U-ban 20N-60 and 3.2 parts of PTS solution.

Thus obtained coating was evaluated as in Example 38 and test results were shown in Table 6.

EXAMPLES 44 TO 47 AND COMPARATIVE EXAMPLE 3

Various coating compositions P-7 to P-10 and P-13 were prepared as in Example 38, by using 50 parts of either one of the resin solutions A-7 to A-10 and B-1 ,32 parts of U-ban 20N-60 and 3.2 parts of PTS solution, respectively. The coatings were prepared as in Example 38 and evaluated. The test results are shown in Table 6.

EXAMPLE 48

50 parts of the resin solution A-1 obtained in Example 22 and 3.4 parts of Sumidule N-3200 (trademark, urethane curing agent, manufactured by Sumitomo Bayer Co.) were taken in a stainless steel vessel, and stirrered and mixed well by means of disper to obtain a coating composition P-11. This was applied onto a tin plate as in Example 38 and baked at 90° C. for 30 minutes.

The coating was evaluated as in Example 38 and test results were shown in Table 6.

EXAMPLE 49

50 parts of the resin solution A-11 obtained in Example 32 and 4.0 parts of Sumidule N-3200 (trademark, urethane curing agent, manufactured by Sumitomo Bayer Co.) were taken in a stainless steel vessel, and stirrered and mixed well by means of disper to obtain a coating composition P-12. This was applied onto a tin plate as in Example 38 and baked at 90° C. for 30 minutes.

The coating was evaluated as in Example 38 and test results were shown in Table 6.

COMPARATIVE EXAMPLE 4

From 60 parts of the resin solution B-2 obtained in Comp. Example 2 and 32 parts of U-ban 20N-60 and 3.2 parts of PTS solution a coating composition P-14 was prepared as in Example 38 and a cured coating was prepared and evaluated as in Example 38.

The test results are shown in Table 6.

EXAMPLES 50 TO 54

As in Example 49, 50 parts of the resin solutions A-12 to A-16 each was taken together with 4.0 parts of Sumidule N-3200 in a stainless steel vessel and mixed and stirrered well by means of disper to obtain coating compositions P-15 to P- 19, respectively. These compositions each was applied onto a tin plate and baked at 90° C. for 30 minutes as in Example 38. Thus obtained coatings were evaluated as in Example 38 and test results were shown in Table 7.

TABLE 2

|  | Example | | | | | | | | | Comp. Ex. | |
| --- | --- | --- | --- | --- | --- | --- | --- | --- | --- | --- | --- |
|  | 23 | 24 | 25 | 26 | 27 | 28 | 29 | 30 | 31 | 1 | 2 |
| porimerizable compound | | | | | | | | | | | |
| a-7 | 90 | 100 | 70 | 70 | | | | | | | |
| a-8 | | | | | 90 | | | | | | |
| a-10 | | | | | | 80 | | | | | |
| b-4 | | | | | | | 70 | | | | |
| c-3 | | | | | | | | 70 | | | |
| d-3 | | | | | | | | | 70 | | |
| monomer | | | | | | | | | | | |
| metyl methacrylate | 10 | | 15 | 15 | 10 | 10 | 15 | 15 | 15 | 30 | 40 |
| n-butyl acrylate | | | 15 | | | 10 | | 15 | 15 | | 35 |
| 2-ethylhexyl acrylate | | | | 15 | | | | | | | |
| 2-hydroxy ethyl methacrylate | | | | | | | | | | | 25 |
| Placcel FM-5* | | | | | | | | | 70 | | |
| Solvent | | | | | | | | | | | |
| Solvesso-100 | 80 | 80 | 80 | 80 | 80 | 80 | 80 | 80 | 80 | 80 | 80 |
| xylene | 20 | 20 | 20 | 20 | 20 | 20 | 20 | 20 | 20 | 20 | 20 |
| Initiator** | 5.5 | 5.5 | 5.5 | 5.5 | 5.5 | 5.5 | 5.5 | 5.5 | 5.5 | 5.5 | 5.5 |
| Polym. temperature (°C.) | 140~150 | 140~150 | 140~150 | 140~150 | 140~150 | 140~150 | 140~150 | 140~150 | 140~150 | 140~150 | 140~150 |
| mole % of poly- | 51.9 | 100 | 23.9 | 26.6 | 21.2 | 24.3 | 21.8 | 21.3 | 23.2 | 25 | 22.2 |

TABLE 2-continued

| | Example | | | | | | | | | Comp. Ex. | |
|---|---|---|---|---|---|---|---|---|---|---|---|
| | 23 | 24 | 25 | 26 | 27 | 28 | 29 | 30 | 31 | 1 | 2 |
| merizable compound | | | | | | | | | | | |

*Daisel Chem. Ind.
**t-butyl peroxy-2-ethylhexanoate
note:
"Mole % of polymerizable compound" in Comp. Ex. 1 and 2 represents mole % of Placcel FM-5 and of 2-hydroxyethylmethacrylate, respectively.

TABLE 3

| | Example | | | | |
|---|---|---|---|---|---|
| | 33 | 34 | 35 | 36 | 37 |
| porimerizable compound | | | | | |
| a-2 | 80 | | | | |
| a-4 | | 90 | | | |
| b-2 | | | 80 | | |
| c-1 | | | | 60 | |
| d-1 | | | | | 50 |
| Monomer | | | | | |
| metyl methacrylate | 10 | 5 | 10 | 20 | 20 |
| n-butyl acrylate | 10 | 5 | 10 | 20 | 30 |
| Solvent | | | | | |
| metylisobutylketon | 80 | 80 | 80 | 80 | 80 |
| xylene | 20 | 20 | 20 | 20 | 20 |
| Initiator* | 5.5 | 5.5 | 5.5 | 5.5 | 5.5 |
| Polym. temperature (°C.) | 90~95 | 90~95 | 90~95 | 90~95 | 90~95 |
| mole % of polymerizable compound | 24.3 | 23.9 | 24.3 | 24.7 | 21.2 |

TABLE 4

| | Example | | | | | | | | | | | Comp. Ex. | |
|---|---|---|---|---|---|---|---|---|---|---|---|---|---|
| | 22 | 23 | 24 | 25 | 26 | 27 | 28 | 29 | 30 | 31 | 32 | 1 | 2 |
| resin solution | A-1 | A-2 | A-3 | A-4 | A-5 | A-6 | A-7 | A-8 | A-9 | A-10 | A-11 | B-1 | B-2 |
| solid content (%) | 90.1 | 90.2 | 89.8 | 89.9 | 90.0 | 85.1 | 90.3 | 89.7 | 90.1 | 90.2 | 90.2 | 90.0 | 75.1 |
| viscosity (at 25° C. Gardner) | $Z_1$ | Y-Z | Y > Z | $Z_1$ | $Z-Z_1$ | $Z_1-Z_2$ | Z | $Z < Z_1$ | $Z-Z_1$ | $Z-Z_1$ | $Z_1-Z_2$ | $Z_1-Z_2$ | $Z_2-Z_3$ |

TABLE 5

| | Example | | | | |
|---|---|---|---|---|---|
| | 33 | 34 | 35 | 36 | 37 |
| resin solution | A-12 | A-13 | A-14 | A-15 | A-16 |
| solid content (%) | 89.7 | 90.2 | 89.8 | 90.0 | 89.9 |
| viscosity (at 25° C. Gardner) | Z | $Z_1-Z_2$ | Y < Z | $Z_2$ | $Z_2-Z_3$ |

TABLE 6

| | Example | | | | | | | | | | | | Comp. Ex. | |
|---|---|---|---|---|---|---|---|---|---|---|---|---|---|---|
| | 38 | 39 | 40 | 41 | 42 | 43 | 44 | 45 | 46 | 47 | 48 | 49 | 3 | 4 |
| thickness (μ) | 60 | 61 | 60 | 59 | 58 | 55 | 59 | 60 | 61 | 59 | 62 | 61 | 60 | 54 |
| finishing appearance (1) | ○ | ○ | ○ | ○ | ○ | ○ | ○ | ○ | ○ | ○ | ○ | ○ | Δ | ○ |
| MEK rubbing (2) | ○ | ○ | ○ | ○ | ○ | ○ | ○ | ○ | ○ | ○ | ○ | ○ | ○ | Δ~X |
| alkali resistance (3) | ○ | ○ | ○ | ○ | ○ | ○ | ○ | ○ | ○ | ○ | ○ | ○ | X | Δ |
| film elongation (%) (4) | 30 | 35 | 40 | 30 | 30 | 35 | 60 | 50 | 30 | 60 | 70 | 70 | 25 | 3 |

TABLE 7

| | Example | | | | |
|---|---|---|---|---|---|
| | 50 | 51 | 52 | 53 | 54 |
| thickness (μ) | 54 | 57 | 60 | 59 | 55 |
| finishing appearance (1) | ○ | ○ | ○ | ○ | ○ |
| MEK rubbing (2) | ○ | ○ | ○ | ○ | ○ |
| alkali resistance (3) | ○ | ○ | ○ | ○ | ○ |
| film elongation (%) (4) | 30 | 40 | 30 | 20 | 20 |

(1) visual evaluation
○: good
Δ: fairly good
X: bad
(2) film surface was rubbed with a gauze impregnated with MEK back and forth 50 times and then surface conditions were visually examined.
○: good
Δ: fairly good
X: bad
(3) 5% KOH was dropped as a spot onto film surface and dried. Thereafter, surface conditions were visually examined.
○: good
Δ: fairly good
X: bad
(4) measured by using Tensilon manufactured by Toyo Boldwin Co.

What is claimed is:
1. A process for preparing a polymerizable compound of the formula:

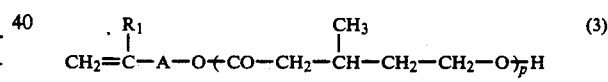

wherein $R_1$ is hydrogen atom or methyl; A represents a group represented by either one of the formula:

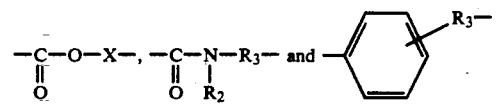

in which X is a group represented by either one of the formula:

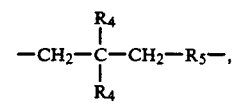

-continued

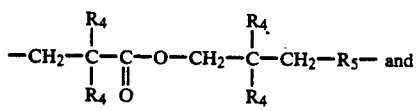

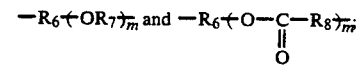

$R_2$ is hydrogen atom or an alkyl having 1 to 10 carbon atoms; $R_3$ is a group represented by either one of the formula:

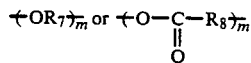

$R_4$ are the same or different radicals and each represents a lower alkyl having 1 to 4 carbon atoms; $R_5$ is a group represented by the formula:

$+OR_7\!\!\!\!\!\xrightarrow{}_{m}$ or $+O-\underset{\underset{O}{\|}}{C}-R_8\!\!\!\!\!\xrightarrow{}_{m}$ $R_6$ is an alkylene having 1 to 4 carbon atoms; $R_7$ is an alkylene having 2 to 4 carbon atoms; $R_8$ is an alkylene having 2 to 7 carbon atoms; m is 0 or an integer of from 1 to 4; and p is an integer of from 1 to 100; the process comprising ring-opening addition polymerizing 1 to 100 moles of β-methyl-δ-valerolactone to one mole of a compound having both polymerizable double bond and hydroxyl group represented by the formula:

 (I)

(in which $R_1$ and A each has the same meaning as defined above) in the presence of a ring-opening addition polymerization catalyst which is a member selected from the group consisting of alkali metals, metal alkoxides and alkyl metal compounds.

2. A process according to claim 1 wherein p is an integer of from 1 to 20.

3. A polymerizable compound represented by the formula:

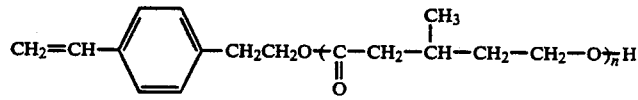

in which n is an integer of from 1 to 100.

4. A polymerizable compound according to claim 3 wherein n is an integer of from 1 to 20.

5. A polymerizable compound represented by the formula:

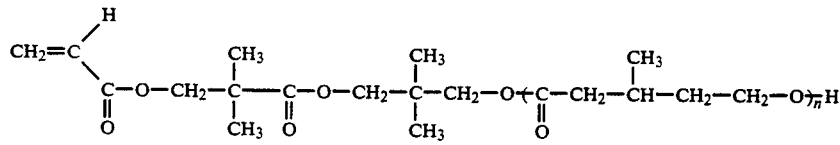

in which n is an integer of from 1 to 100.

6. A polymerizable compound according to claim 5 wherein n is an integer of from 1 to 20.

7. A polymerizable compound represented by the formula:

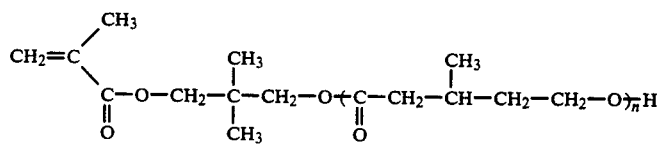

in which n is an integer of from 1 to 100.

8. A polymerizable compound according to claim 7 wherein n is an integer of from 1 to 20.

9. A polymerizable compound represented by the formula:

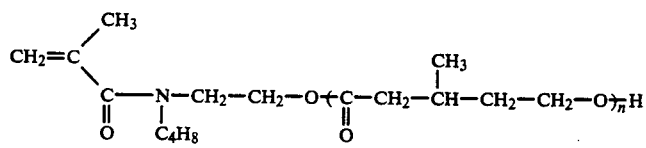

in which n is an integer of from 1 to 100.

10. A polymerizable compound according to claim 9 wherein n is an integer of from 1 to 20.

* * * * *